(12) United States Patent
Enzelberger

(10) Patent No.: US 9,404,929 B2
(45) Date of Patent: Aug. 2, 2016

(54) METHODS FOR IDENTIFICATION OF AN ANTIBODY OR A TARGET

(75) Inventor: Markus Enzelberger, Planegg (DE)

(73) Assignee: Morpho Sys AG, Martinsried (DE)

( * ) Notice: Subject to any disclaimer, the term of this patent is extended or adjusted under 35 U.S.C. 154(b) by 12 days.

(21) Appl. No.: 12/865,884

(22) PCT Filed: Feb. 11, 2009

(86) PCT No.: PCT/EP2009/000953
§ 371 (c)(1),
(2), (4) Date: Aug. 3, 2010

(87) PCT Pub. No.: WO2009/100896
PCT Pub. Date: Aug. 20, 2009

(65) Prior Publication Data
US 2010/0330577 A1 Dec. 30, 2010

Related U.S. Application Data

(60) Provisional application No. 61/027,507, filed on Feb. 11, 2008, provisional application No. 61/045,039, filed on Apr. 15, 2008.

(30) Foreign Application Priority Data

Feb. 11, 2008 (EP) .................................... 08151276

(51) Int. Cl.
*G01N 33/68* (2006.01)
*C12N 15/10* (2006.01)

(52) U.S. Cl.
CPC ........ *G01N 33/6854* (2013.01); *C12N 15/1034* (2013.01); *C12N 15/1089* (2013.01)

(58) Field of Classification Search
CPC .............. G01N 2500/00; G01N 33/68; G01N 33/6854; G01N 33/6857
IPC ..................................................... G01N 33/68
See application file for complete search history.

(56) References Cited

U.S. PATENT DOCUMENTS

| | | | |
|---|---|---|---|
| 6,297,053 B1 | 10/2001 | Stemmer | |
| 6,897,028 B1 | 5/2005 | Makowski et al. | |
| 7,117,096 B2 | 10/2006 | Luo | |
| 7,288,249 B2 | 10/2007 | Carter et al. | |
| 8,143,007 B2 * | 3/2012 | Devinder et al. | 435/6.12 |
| 2001/0049107 A1 | 12/2001 | Sharon | |
| 2005/0037358 A1 | 2/2005 | Muyldermans | |
| 2005/0170351 A1 | 8/2005 | Tan | |
| 2006/0141532 A1 | 6/2006 | Ferrone et al. | |
| 2006/0188896 A1 | 8/2006 | Seul | |
| 2007/0185656 A1 | 8/2007 | Schadt | |
| 2008/0003566 A1 | 1/2008 | Vaux | |
| 2010/0035241 A1 | 2/2010 | Achatz | |

FOREIGN PATENT DOCUMENTS

| | | |
|---|---|---|
| EP | 2088432 | 8/2009 |
| WO | WO03/052416 | 6/2003 |
| WO | WO2004/094474 | 11/2004 |
| WO | WO 2004/094474 | * 11/2004 |
| WO | WO2005/094159 | 10/2005 |
| WO | WO2006/014498 | 2/2006 |
| WO | PCT/EP2009/000953 | 2/2009 |
| WO | 2009100896 | 8/2009 |

OTHER PUBLICATIONS

Wang, X et al. Journal of Immunological Methods 244 (2000) 217-225.*
Gabor et al. Biotechnology Journal (2007) vol. 2, pp. 201-206.*
Glanville et al., Proc Natl Acad Sci 1;106(48):20216-21 (Dec. 2009).
Mortavazi et al; Pak J Biol Sci. Apr. 15, 2008;11(8):1142-62008.
Reddy et al. Pak J Biol Sci. Aug. 15, 2010;13(16):794-801. 2010.
Salehi et al., Isoform discovery by targeted cloning, deep well pooling and parallel sequencing, Nature Methods, 5(7):597-600 (2008).
Scanlan et al., Humoral Immunity to human breast cancer: antigen definition and quantitative analysis of mRNA expression, Cancer Immunity, 1:4 (2001).
Maecker et al., Linking Genomics to Immunotherapy by Reverse Immunology-Immunomics in the New Millenium, Current Molecular Medicine, 7:609-619 (2001).
Winter et al., Ann.Rev.lmmunol., 12:433-455(1994).
Iwasaki Y. et al. Struture profile of idiotype, anti-idiotype and anti-anti-idiotype monoclonal antibodies in the HLA-DQ3 antigenic system, Eur. J. Immunol., 24: 2874-2881 (1994).
Margulies, et al.: "Genome sequencing in microfabricated high-density picolitre reactors", Nature, vol. 437, 2005.
Roche "Genome Sequencer System Application Note No. 5, 2007, Amplicon Sequencing" , 2007.
Wickipedia "Immunoassay" , 2016.
Shendure, et al.: "Accurate multiplex polony sequencing of an evolved bacterial genome" , Science, vol. 309, 2005.
Hall "Advanced sequencing technologies and their wider impact in microbiology" , The Journal of Experimental biology, vol. 209, 2007.
Boudinot, et al.: "New perspectives for large-scale repertoire analysis of immune receptors" , Molecular Immunology, vol. 45(9), 2008.
Benichou, et al.: "Rep-Seq: uncovering the immunological repertoire through next-generation sequencing" , Immunology, vol. 135(3), 2012.
Fischer "Sequencing Antibody Repertoires: The next Generation" mAbs, vol. 3.1, 2011.
National Human Genome Research Institute, "International Consortium Completes Human Genome Project" , 2003.
Shendure: Next-generation DNA sequencing, nature Biotechnology, vol. 26, 2008.
Roche, "454 Life Sciences Unveils New Bench Top Sequencer, Significant Improvements to the Genome Sequencer FLX System Including 1,000 by Reads for 2010" 2009.
Liu, et al.: "Comparison of Next-Generation Sequencing Systems" Journal of Biomedicine and Biotechnology, vol. 2012, 2012.
Morozova, et al.: "Applications of next-generation sequencing technologies in functional genomics" , Genomics, vol. 92, 2008.

* cited by examiner

*Primary Examiner* — Mary Zeman
(74) *Attorney, Agent, or Firm* — Paul F. Wiegel

(57) ABSTRACT

This disclosure relates to methods for identifying an antibody, a target molecule, or an agent by analyzing the immunoglobulin repertoire sequence data in a sample and by determining the most dominant VH and VL chains present in said sample, as well as materials used therewith.

12 Claims, No Drawings

METHODS FOR IDENTIFICATION OF AN ANTIBODY OR A TARGET

CROSS-REFERENCE TO RELATED APPLICATION

This application claims the benefit of U.S. provisional application Ser. No. 61/045,039 filed Apr. 15, 2008 and U.S. provisional application Ser. No. 61/027,507 filed Feb. 11, 2008, which are both incorporated by reference in their entireties.

FIELD

This disclosure relates to methods for identifying an antibody, a target molecule, or an agent by analyzing the sequence data of the immunoglobulins in a biological sample and by determining the most abundant VH and VL chains present in said biological sample. Materials used therewith also are provided.

BACKGROUND

Current methods for identifying an antibody or a target molecule involve laborious processes of isolating antibodies from activated human B-cells. For example, isolation of fully human antibodies from B-cells of immunized or cancer patients is considered as an advantageous route to fully human antibodies. Several companies provide commercial services for isolating single B-cells from humans. These B-cells are either immortalized or the genetic information of the immunoglobulins of the single cells is recovered. Such methods may involve laborious and expensive high-throughput techniques, including techniques for isolating genetic information cell by cell, immortalizing thousands of cells and screening their respective output on the target tissue.

Since recently several companies offer whole genome sequencing services, or machines that can be used to accomplish respective tasks. This includes include Roche's 454 system, Illuminas's Solexa system, and Helico Biosciences Heliscope system. Helico's, for example, can sequence 2×109 bases in 24 hours with a single machine by also keeping quantitative distribution of target sequences.

U.S. Pat. No. 7,288,249 discloses a method for identifying an antigen which is differentially expressed on the surface of two or more distinct cell populations. Immunization triggers B cells to make a VH-VL combination that binds the immunogen to proliferate (clonal expansion) and to secrete the corresponding antibody. The process according to U.S. Pat. No. 7,288,249 however involves cloning of the VH and VL genes (the VH and the VL genes are cloned separately by polymerase chain reaction (PCR)), and the VH and the VL genes are recombined randomly in phage libraries (i.e. there is no selection of the most abundant VH and VL genes), which is then searched for antigen-binding clones as described in Winter et al., *Ann. Rev. Immunol.*, 12: 433-455 (1994). Nucleic acid encoding antibody variable gene segments (including VH and VL segments) are recovered from the cells of interest and amplified. In the case of rearranged VH and VL gene libraries, the desired DNA is obtained by isolating genomic DNA or mRNA from lymphocytes followed by polymerase chain reaction (PCR) with primers matching the 5' and 3' ends of rearranged VH and VL genes. To find useful antibodies, the naive antibody phage library is screened against live cancer cells.

U.S. Pat. No. 6,897,028 describes a method for identification of molecular targets in which a protein binds to a ligand, screening the ligand against a peptide or protein library wherein the peptide or protein members of the library are selected from expression products of a cDNA library derived from a cell and fragments of those expression products. The process also involves determining the nucleic acid sequence which encode the members which have been separated from the library and translating these nucleic acid sequences into peptide sequences and identifying the protein.

U.S. Publication No. 20060141532 (application Ser. No. 11/286,917) discloses methods for identifying and designing immunogenic peptides by using a protocol for determining the amino acid sequence of certain VH or VL regions of an anti-idiotypic antibody as disclosed in Iwasaki, et al. *Eur. J. Immunol.*, 24:2874-2881, 1994. The amino acid sequence of the antigen is determined by standard amino acid analysis techniques or by chemical sequencing; the amino acid sequence of VH and/or VL regions of the anti-idiotypic antibody are determined by sequencing the genomic DNA or cDNA encoding the respective region according to techniques known in the art.

WO2005/094159 describes the isolation of binding peptides from immortalized lymphocytes and the testing of these binding peptides, usually immunoglobulins of the type IgM, for selective binding to tumor tissue, but not healthy tissue. The binding peptide may inhibit proliferation of tumors.

WO03/052416 describes an approach for the isolation and sequencing of candidate VH and VL sequences from B cells. The immunoglobulins encoded by said candidate VH and VL sequences are potentially useful in the treatment of infections. The methodology described in WO03/052416, as well as all others methods disclosed in the prior art, require the manipulation of the nucleic acids prior to sequencing. In particular time consuming cloning steps are necessary which make it impossible to practice the method in a scale as disclosed in the present to invention.

As is the case for WO03/052416, all the methods discussed above involve laborious process of isolating nucleic acids encoding a target and/or genomic sequencing by ultra high-throughput techniques. However, a less laborious, cost effective and/or easier method for identifying a target molecule by analyzing sequence data of the VH and VL chains and by determining the most dominant VH and VL would be advantageous.

SUMMARY

Embodiments of this disclosure relate generally to methods for identifying an antibody, a target molecule, or an agent by analyzing the sequence data of the variable heavy (VH) and variable light (VL) chains of the immunoglobulins present in a biological sample. Some of the embodiments herein relate to determining the most abundant VH and VL chains present in a sample using a predetermined computer-implemented algorithm, synthesizing polynucleotides of the most abundant VH and VL chains for expression in a vector, and testing the expressed antibodies to identify the target molecule. Other embodiments relate to determining the most abundant VH and VL chains present in a sample using a predetermined computer-implemented algorithm, synthesizing polynucleotides of the most abundant VH and VL chains for expression in a vector, and testing which of the expressed antibodies bind to a certain target molecule or target tissue. In certain embodiments the sample is a biological sample which is not pre-selected or pre-enriched.

One embodiment provides methods of identifying an antibody, a target, or an agent in a sample comprising: a) obtaining cDNAs of mRNAs encoding immunoglobulins in a sample, thereby obtaining a mixture of cDNAs; b) sequencing each of the variable heavy (VH) and variable light (VL) chains of the immunoglobulins, thereby obtaining sequence data of the VH and VL chains of the immunoglobulins present in the sample; c) determining the most abundant VH and VL chains present in the sample using a predetermined computer-implemented algorithm; d) synthesizing polynucleotides of the most abundant VH and VL chains and producing antibodies using a mammalian expression vector; and e) testing the antibodies, thereby identifying an antibody which binds to a certain target molecule or tissue or identifying a target molecule which binds to a certain antibody.

Another embodiment provides methods of identifying an antibody, a target, or an agent comprising: a) providing a biological sample from a mammal, such as human, murine, rodent, mouse, rat, squirrel, chipmunk, gopher, porcupine, beaver, hamster, gerbil, guinea pig, rabbit, dog, cat, cow, or horse, that is immunized or infected with an agent or a target molecule; b) harvesting B-cells from the biological sample; c) obtaining mRNAs encoding immunoglobulins (for example, IgGs) in the harvested B-cells; d) generating cDNAs of the immunoglobulins (for example, by reverse transcriptase-PCR and using IgG specific primers for amplification), thereby obtaining a mixture of the cDNAs; e) sequencing each of the variable heavy (VH) and variable light (VL) chains of the immunoglobulins (for example, by obtaining independent sequences of VH and VL), thereby obtaining sequence data of the VH and VL chains of the immunoglobulins present in the sample; f) analyzing the sequence data of the VH and VL chains to determine the most dominant VH and VL chains present in the sample; g) determining the most abundant VH and VL chains present in the sample using a predetermined computer-implemented algorithm; h) synthesizing polynucleotides of the most abundant VH and VL chains; i) integrating the synthesized VH and VL polynucleotides into a mammalian expression vector; j) allowing the VH and VL polynucleotides-integrated vectors to express in a culture medium, thereby producing antibodies or fragments thereof; and k) testing the antibodies by using an immunoassay, thereby identifying the antibody, target molecule, or the agent to the target molecule. In certain embodiments the mammal is a diseased mammal.

In certain embodiments the immunoglobulin is of any one of the immunoglobuline classes IgG, IgM, IgA, IgD or IgE, or a fragment thereof. In some embodiments the immunoglobulin is of the class IgG.

In certain embodiments the immunoglobulin is of any one of the immunoglobuline G subclasses IgG1, IgG2, IgG3 or IgG4.

Another embodiment provides methods of identifying an antibody, a target, or an agent, wherein the cDNAs of the immunoglobulins are generated by reverse transcriptase-PCR.

Another embodiment provides methods of identifying an antibody, a target, or an agent, wherein IgG specific primers are used in the reverse transcriptase-PCR amplification.

Another embodiment provides methods of identifying an antibody, a target, or an agent, wherein primers are used in the reverse transcriptase-PCR amplification which are specific for any one of the immunoglobuline G subclasses IgG1, IgG2, IgG3 or IgG4.

Another embodiment provides methods of identifying an antibody, a target, or an agent, wherein independent sequence data for the VH and VL chains of the immunoglobulins are obtained. Sequence data of the VH and VL chains are stored in a database and the most abundant VH and VL chains are determined via a computer-implemented algorithm.

Another embodiment provides methods of identifying an antibody, a target, or an agent, wherein the mammal is a human, murine, rodent, mouse, rat, squirrel, chipmunk, gopher, porcupine, beaver, hamster, gerbil, guinea pig, rabbit, dog, cat, cow, or horse.

Another embodiment provides methods of identifying an antibody, a target, or an agent in a sample comprising the steps of: a) analyzing the sequence data of the VH and VL chains present in the sample; and b) determining the abundance of VH and VL chains present in the sample. The methods further comprising preparing one or more immunoglobulins containing abundant VH and VL chains identified in step b).

In certain embodiments the human is a cancer patient, or is immunized or is infected with an agent or a target molecule.

Yet, another embodiment of this disclosure provides methods of identifying an antibody, a target, or an agent, wherein the mammal is a human, murine, rodent, mouse, rat, squirrel, chipmunk, gopher, porcupine, beaver, hamster, gerbil, guinea pig, rabbit, dog, cat, cow, or horse.

DETAILED DESCRIPTION

This disclosure provides methods for identifying an antibody, a target molecule, or an agent by analyzing the immunoglobulin sequence data of the variable heavy (VH) and variable light (VL) chains present in a biological sample, as well as materials used in the methods disclosed herein. This disclosure also pertains to methods of determining the most abundant VH and VL chains present in a sample using a predetermined computer-implemented algorithm, synthesizing polynucleotides of the most abundant VH and VL chains for expression in a vector, and testing the expressed antibodies to identify the target molecule.

According to one aspect, this disclosure provides methods for identifying or detecting an antibody, a target molecule, or an agent by sequencing the "immunonome", which refers to the complete mRNA (or cDNA after reverse transcription-PCR) encoding immunoglobulins (such as IgGs), in a mammalian sample (such as human, murine, or rodent, mice, rats, squirrels, chipmunks, gophers, porcupines, beavers, hamsters, gerbils, guinea pigs, rabbits, dogs, cats, cows, or horses), wherein the mammal has been immunized with a target molecule, is a cancer patient or is infected with a certain viral, bacterial or protozoan species. In certain embodiments the mammal (for example, human, murine, or rodent, mice, rats, squirrels, chipmunks, gophers, porcupines, beavers, hamsters, gerbils, guinea pigs, rabbits, dogs, cats, cows, or horses) is immunized with a target molecule, such as a vaccine. In other embodiments the mammal is a cancer patient.

According to another aspect, B-cells are isolated from an immunized mammal or cancer patient, mRNA is extracted from the respective sample, and the immunoglobulins encoded by the mRNA are reverse transcribed and sequenced. In some embodiments, at least $10^4$ B-cells are isolated from the immunized mammal or cancer patient, in other embodiments at least $10^5$ B-cell; $10^6$ B-cells; or even $10^7$ B-cells are isolated from the immunized mammal or cancer patient. Genes encoding immunoglobulin variable chains typically have a length of about 1000 nucleotides. Therefore sequencing of about $2 \times 10^9$ bases of sequence information covers the entire immunonome at least two fold. The dominant CDR sequences, as well as (hyper)mutations thereof, are identified. These sequences are specific, or at least representative for the immunological stimulus. Heavy and light chain sequences (which can't be recovered together) are clustered according to the frequency of dominance, i.e. by their abundance. The most abundant VH and VL sequences are synthesized and transferred (one by one or in mass) into a mammalian expression vector. Vectors are expressed in a suitable medium and screened to obtain immunoglobulins, or fragments thereof, for specificity against the target of interest. The obtained binders are tested for their therapeutic efficacy and can be produced for use as drugs or used to identify new antibodies or molecular targets.

Embodiments of this disclosure provide advantages, including:

Embodiments described herein can replace the ultra high-throughput wet biology with bioinformatics and single, massive parallel molecule sequencing technology which enables parallelization in analyzing B-cells from many patients in significantly reduced timelines (usually only shotgun sequencing, yielding comparably short stretches of 75-500 base pairs, is performed and assembly is done by alignment of the obtained fragments).

The high homology in the constant regions of the immunoglobulins does not interfere with the alignment algorithms.

The embodiments described herein permit avoidance of cloning steps.

Embodiments described herein, can overcome the problem of isolation of low quality IgMs by using IgG selective primers, IgG subclass specific primers.

The methods herein permit using the immunonome for diagnostic methods. For example, patients suffering from allergies against identical allergens might show similar sequence patterns in their immune response. In principle, therefore, the use of an immunonome profile as biomarker is also feasible if a data set of sufficient size is obtained.

Knowledge of the immunonome also can facilitate design of synthetic, fully human, murine or rodent antibody libraries.

According to one embodiment of this disclosure, an antibody, a target molecule, a disease marker, an agent or an agent for a target molecule in a sample, for example, in a biological sample from a mammal (for example, human, murine, or rodent, mice, rats, squirrels, chipmunks, gophers, porcupines, beavers, hamsters, gerbils, guinea pigs, rabbits, dogs, cats, cows, or horses) that is immunized or infected with an agent or a target molecule, is identified, determined, detected or diagnosed by a method comprising the steps of: a) obtaining cDNAs of mRNAs encoding immunoglobulins in the sample (for example, by harvesting B-cells from the sample), thereby obtaining a mixture of the cDNAs; b) sequencing each of the variable heavy (VH) and variable light (VL) chains of the immunoglobulins, thereby obtaining sequence data of the VH and VL chains of the immunoglobulins (such as IgGs) present in the sample; c) determining the most abundant VH and VL chains present in the sample (e.g., by analyzing sequence data of the VH and VL chains present in the sample using a predetermined computer-implemented algorithm); d) synthesizing polynucleotides of the most abundant VH and VL chains and producing antibodies using a mammalian expression vector (for example, by integrating the synthesized VH and VL polynucleotides into the mammalian expression vector); and e) testing the antibodies (for example, by employing an immunoassay), thereby identifying the antibody, target, or the agent to target molecule in the sample.

According to another embodiment of this disclosure, an antibody, a target molecule, a disease marker, an agent or an agent for a target molecule is identified, determined, detected or diagnosed by a method comprising the steps of: a) providing a biological sample from a mammal (for example, human, murine, or rodent, mice, rats, squirrels, chipmunks, gophers, porcupines, beavers, hamsters, gerbils, guinea pigs, rabbits, dogs, cats, cows, or horses) that is immunized or infected with an agent or a target molecule or the sample containing the disease marker or antibodies to a target molecule; b) harvesting B-cells from the biological sample; c) obtaining mRNAs encoding immunoglobulins in the harvested B-cells; d) generating cDNAs of the immunoglobulins, thereby obtaining a mixture of the cDNAs; e) sequencing each of the variable heavy (VH) and variable light (VL) chains of the immunoglobulins (preferable the sequences of VH and VL and obtained independently), thereby obtaining sequence data of the VH and VL chains of the immunoglobulins (such as IgGs) present in the sample; f) analyzing the sequence data of the VH and VL chains to determine the most dominant VH and VL chains present in the sample; g) determining the most abundant VH and VL chains present in the sample using a predetermined computer-implemented algorithm; h) synthesizing polynucleotides of the most abundant VH and VL chains; i) integrating the synthesized VH and VL polynucleotides into a mammalian expression vector; j) allowing the VH and VL polynucleotides-integrated vectors to express in a culture medium, thereby producing antibodies; and k) testing the antibodies by using an immunoassay, thereby identifying the antibody, target, target molecule, disease marker, agent or the agent for the target molecule.

In embodiments of this disclosure, the mRNAs encoding the immunoglobulin are of the class IgG.

In other embodiments of this disclosure, the cDNAs of the immunoglobulins are generated by reverse transcriptase-PCR.

According to other embodiments of this disclosure, the IgG specific primers are used in the reverse transcriptase-PCR amplification.

In other embodiments of this disclosure, the independent sequence data for the VH and VL chains of the immunoglobulins are obtained for determining the computer-implemented algorithm.

In another embodiment of this disclosure, the mammal is a human, murine, or rodent, mouse, rat, squirrel, chipmunk, gopher, porcupine, beaver, hamster, gerbil, guinea pig, rabbit, dogs, cat, cow, or horse.

According to another embodiment of this disclosure, an antibody, a target molecule, a disease marker, an agent or an agent for a target molecule is identified, determined, detected or diagnosed by a method comprising the steps of:

a) analyzing the sequence data of the VH and VL chains present in the sample; and b) determining the abundance of VH and VL chains present in the sample.

In another embodiment the method, further comprises preparing one or more immunoglobulins containing abundant VH and VL chains identified in step b). In other embodiments of this disclosure the sample is a biological sample. In other embodiments the biological sample is from a mammal. In yet other embodiments said mammal is a human, murine, rodent, mouse, rat, squirrel, chipmunk, gopher, porcupine, beaver, hamster, gerbil, guinea pig, rabbit, dog, cat, cow, or horse. In other embodiments said human is a cancer patient, or is immunized or is infected with an agent or a target molecule. In other embodiments the immunoglobulins are of the class IgG.

DEFINITIONS AND OTHER EMBODIMENTS OF THE DISCLOSURE

The term "immunoglobulin (Ig)" refers to a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (Ig) domain" herein is meant a region of an immunoglobulin that exists as a distinct structural entity as ascertained by one skilled in the art of protein structure. The term "IgG" as used herein is meant a protein belonging to the class of antibodies that are substantially encoded by a recognized immunoglobulin gamma gene.

The term "antibodies" includes polyclonal antibodies, affinity-purified polyclonal antibodies, monoclonal antibodies, fully human, murine or rodent antibodies, and antigen-binding fragment, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. An antibody according to this disclosure may be substantially encoded by immunoglobulin genes belonging to any of the antibody classes. The antibody comprises sequences belonging to the IgG class of antibodies, including human subclasses IgG1, IgG2, IgG3, and IgG4. The instant antibody comprises sequences belonging to the IgA (including human subclasses IgA1 and IgA2), IgD, IgE, IgG, or IgM classes of antibodies.

The term "variable chain" or the "variable region" as used herein means the region of an immunoglobulin that comprises one or more Ig domains substantially encoded by any of the VL (including $V_\kappa$ and $V_\lambda$), VH, JL (including $J_\kappa$ and $J_\lambda$), and JH genes that make up the light chain (including kappa and lamda) and heavy chain immunoglobulin genetic loci respectively. A light or heavy chain variable region (VL and VH) consists of a "framework" or "FR" region interrupted by three hypervariable regions referred to as "complementarity determining regions" or "CDRs." The extent of the framework region and CDRs have been precisely defined (see Kabat, 1991, *J. Immunol.*, 147, 915-920.; Chothia & Lesk, 1987, *J. Mol. Biol.* 196: 901-917; Chothia et al., 1989, Nature 342: 877-883; Al-Lazikani et al., 1997, *J. Mol. Biol.* 273: 927-948). The framework regions of an antibody, that is the combined framework regions of the constituent light and heavy chains, serves to position and align the CDRs, which are primarily responsible for binding to an antigen.

The term "biological sample" may refer to any sample of biological origin, including tissue or fluid, whole blood, serum or plasma samples, or a sample that contains any components such as protein, polypeptides, nucleic acids or polynucleotides. In certain embodiments the biological sample is from a mammal, such as from human, murine, or rodent, mice, rats, squirrels, chipmunks, gophers, porcupines, beavers, hamsters, gerbils, guinea pigs, rabbits, dogs, cats, cows, or horses. In other embodiments the biological sample is from a mammal, wherein the mammal (for example, human, murine, or rodent, mice, rats, squirrels, chipmunks, gophers, porcupines, beavers, hamsters, gerbils, guinea pigs, rabbits, dogs, cats, cows, or horses) is immunized with a target molecule, is a cancer patient or is infected with a certain viral, bacterial or protozoan species.

A "target" or "target molecule" refers to a molecule that is reactive with or binds to an immunoglobulin, such as an antibody. The target may be known unknown and/or can be identified by methods known in the art e.g. immunoprecipitation with subsequent mass spectrometric analysis, N-terminal protein sequencing etc.

The term "mammal" refers to any organism classified as a mammal, for example, human, murine, or rodent, mice, rats, squirrels, chipmunks, gophers, porcupines, beavers, hamsters, gerbils, guinea pigs, rabbits, dogs, cats, cows, and horses. In embodiments, the mammal is a mouse. In other embodiments of this disclosure, the mammal is a human or a rat.

The sequence information can be stored in any format and thus the term "database" as used herein refers to any collection of information, in particular sequence information, such as a database file, a lookup table, an Excel spreadsheet or the like. In certain embodiments the database is stored in electronic form, such as a computer readable memory device. This includes media such as a server, a client, a hard disk, a CD, a DVD, a personal digital assistant such as a Palm Pilot, a tape, a zip disk, the computer's internal ROM (read-only-memory) or the internet or worldwide web. Other media for the storage of files accessible by a computer will be obvious to one skilled in the art.

"Computer-implemented algorithm" as used in this context refers to any statistical means that can be used determine which VH and VL chains are most abundant in a certain biological sample. Such computer-implemented algorithm may be part of a larger software package or a stand-alone software patch or application. The computer-implemented algorithm typically works on a database containing sequence data of variants of VH and VL chains. The output of the computer-implemented algorithm is typically a list of the most dominant or abundant sequences, for example, individual VH or VL chains, present in a biological sample.

According to embodiments of this disclosure, the most dominant or abundant sequences identified via the computer-implemented algorithm are synthesized and integrated into an expression vector for expression as described herein.

The term "(poly)peptide" relates to molecules consisting of one or more chains of multiple, i.e. two or more, amino acids linked via peptide bonds.

The term "protein" refers to (poly)peptides where at least part of the (poly)peptide has or is able to acquire a defined three-dimensional arrangement by forming secondary, tertiary, or quaternary structures within and/or between its (poly)peptide chain(s). This definition comprises proteins such as naturally occurring or at least partially artificial proteins, as well as fragments or domains of whole proteins, as long as these fragments or domains are able to acquire a defined three-dimensional arrangement as described above. Examples of (poly)peptides/proteins consisting of one chain are single-chain Fv antibody fragments, and examples for (poly)peptides/proteins consisting of more chains are Fab antibody fragments.

In certain embodiments, the disclosure provides libraries of (poly)peptides comprising at least parts of members or derivatives of the immunoglobulin superfamily, preferably of the immunoglobulins, such as immunoglobulins of the class IgG. Some embodiments provide libraries of human antibodies. Other embodiments provide libraries of mammalian or rodent antibodies. The variable heavy and light chain regions preferably comprise framework regions (FR) 1, 2, 3, and 4 and complementary determining regions (CDR) 1, 2, and 3.

These artificial genes encoding the most abundant VH and VL chains are then constructed, e.g. by total gene synthesis or by the use of synthetic genetic subunits. These genetic subunits may correspond to structural sub-elements on the (poly)peptide level, e.g. to one or more framework region and/or to one or more complementary determining region. On the DNA level, these genetic subunits may be defined by cleavage sites at the start and the end of each of the sub-elements, which are unique in the vector system. In certain embodiments the sub-elements are compatible with the HuCAL (Human Combinatorial Antibody) Library, as described in U.S. Pat. No. 7,264,963.

This collection of DNA molecules can then be used to create libraries of antibodies or antibody fragments, such as Fv, disulphide-linked Fv, single-chain Fv (scFv), or Fab fragments, which may be used as sources of specificities against new target antigens. Moreover, the affinity of the antibodies can be optimized using pre-built library cassettes and know maturation procedure.

The disclosure provides a method for identifying one or more genes encoding one or more antibodies or antibody fragments which binds to a target, comprising to the steps of expressing the antibodies or the antibody fragments, and then screening them to isolate one or more antibodies or antibody fragments which bind to a given target molecule.

Gene expression: The term "gene expression" refers to in vivo or in vitro processes, by which the information of a gene is transcribed into mRNA and then translated into a protein/(poly)peptide. Thus, the term gene expression refers to a process which occurs inside cells, by which the information of a gene is transcribed into mRNA and then into a protein. The term expression also includes all events of post-translational modification and transport, which are necessary for the (poly)peptide to be functional. Analysis of homologous genes: The corresponding amino acid sequences of two or more genes are aligned to each other in a way which maximizes the correspondence between identical or similar amino acid residues at all positions. These aligned sequences are termed homologous if the percentage of the Sum of identical and/or similar residues exceeds a defined threshold.

The term "vector" refers to a nucleic acid molecule capable of transporting between different genetic environments another nucleic acid to which it has been operatively linked. Preferred vectors are those capable of autonomous replication and/or expression of nucleic acids to which they are linked. Vectors capable of directing the expression of genes to which they are operatively linked are referred to herein as "expression vectors." The choice of the vector depends on the specific requirements and the functional properties of a given vector.

In one embodiment of this disclosure, the vector includes a procaryotic replicon i.e., a DNA sequence having the ability to direct autonomous replication and maintenance of the recombinant DNA molecule extra chromosomally in a procaryotic host cell, such as a bacterial host cell, transformed therewith. Such replicons are well known in the art. In addition, those embodiments that include a procaryotic replicon also include a gene whose expression confers a selective advantage, such as drug resistance, to a bacterial host transformed therewith.

Vectors that include a procaryotic replicon can also include a procaryotic promoter capable of directing the expression (transcription and translation) of the $V_H$- and/or $V_L$-coding homologs in a bacterial host cell, such as *Escherichia coli* transformed therewith. A promoter is an expression control element formed by a DNA sequence that permits binding of RNA polymerase and transcription to occur. Promoter sequences compatible with bacterial hosts are typically provided in plasmid vectors containing convenience restriction sites for insertion of a DNA segment. Examples of such vector plasmids include pUC8, pUC9, pBR322, and pBR329, pPL and pKK223, available commercially. Such vectors are referred to as "prokaryotic expression vectors".

Preferable eucaryotic expression vectors include those are compatible with vertebrate cells. The term "eucaryotic expression vector" refers to any expression vector useful in the expression of nucleic acids in eucaryotic host cells. In particular embodiment of this disclosure, the eukaryotic vectors are mammalian expression vectors. The term "mammalian expression vector" refers to any expression vector useful in the expression of nucleic acids in mammalian host cells.

Eucaryotic expression vectors are well known in the art and also are available commercially. Typically, such vectors are provided containing convenient restriction sites for insertion of the desired DNA homologue. Examples of such vectors include $pSV_L$ and pKSV-10, pBPV-1/PML2d, and pTDT1 (ATCC, No. 31255).

In another embodiment of this disclosure, the eucaryotic expression vectors include a selection marker that is effective in an eucaryotic cell, preferably a drug resistant selection marker. A preferred drug resistance marker is the gene whose expression results in neomycin resistance, i.e., the neomycin phosphotransferase (neo) gene. Southern et al., *J. Mol. Appl. Genet.*, 1:327-341 (1982).

Retroviral expression vectors to express the genes of the $V_H$- and/or $V_L$-coding DNA homologs are also contemplated. The term "retroviral expression vector" refers to a DNA molecule that includes a promoter sequences derived from the long terminal repeat (LTR) region of a retrovirus genome.

$V_H$- and/or $V_L$-coding DNA construct(s) is/are introduced into an appropriate host to provide amplification and/or expression of the $V_H$- and/or $V_L$-coding DNA homologs, either separately or in combination. When the $V_H$ and $V_L$ polypeptides are expressed in different organisms, the respective polypeptides are isolated and then combined in an appropriate medium to form an antibody, or a fragment thereof. Cellular hosts into which a $V_H$- and/or $V_L$-coding DNA homolog-containing construct has been introduced are referred to herein as having been "transformed" or as "transformants."

Host cells can be either procaryotic or eucaryotic. Bacterial cells are preferred procaryotic host cells and typically are a strain of *Escherichia Coli* (*E. coli*) such as, for example, the *E. coli* strain DH5 available from Bethesda Research Laboratories, Inc., Bethesda, Md. Preferred eucaryotic host cells include yeast and mammalian cells including murine and rodents, preferably vertebrate cells such as those from a mouse, rat, monkey or human cell line.

Transformation of appropriate cell hosts with a recombinant DNA molecule is accomplished by methods that typically depend on the type of vector used. With regard to transformation of procaryotic host cells, see, for example, Cohen et al., *Proceedings National Academy of Science*, USA, Vol. 69, P. 2110 (1972); and Maniatis et al., Molecular Cloning, a Laboratory Manual, Cold spring Harbor Laboratory, Cold Spring Harbor, N.Y. (1982). With regard to the transformation of vertebrate cells with retroviral vectors containing rDNAs, see for example, Sorge et al., *Mol. Cell. Biol.*, 4:1730-1737 (1984); Graham et al., *Virol.*, 52:456 (1973); and Wigler et al., *Proceedings National Academy of Sciences, USA*, Vol. 76, P. 1373-1376 (1979).

Screening for expression of $V_H$ and/or $V_L$ polypeptides: Successfully transformed cells, i.e., cells containing a $V_H$- and/or $V_L$-coding DNA homolog operatively linked to a vector, can be identified by any suitable well known technique for detecting the binding of a receptor to a ligand or the presence of a polynucleotide coding for the receptor, preferably its active site. In one embodiment, screening assays are carried out such that the binding of ligand by the receptor produces a detectable signal, either directly or indirectly. Such signals include, for example, the production of a complex, formation of a catalytic reaction product, the release or uptake of energy, and the like. Cells from a population subjected to transformation with a subject recombinant DNA can be cloned to produce monoclonal colonies, for example. Cells form those colonies can be harvested, lysed and their DNA content examined for the presence of the recombinant DNA using a method known in the art, for example, as described in Southern, *J. Mol. Biol.*, 98:503 (1975) or Berent et al., *Biotech.* 3:208 (1985).

Besides direct assaying for the presence of a $V_H$- and/or $V_L$-coding DNA, successful transformation also can be confirmed by well known immunological methods, especially when the $V_H$ and/or $V_L$ polypeptides produced contain a pre-selected epitope. Samples of cells suspected of being transformed are assayed for the presence of the pre-selected epitope using an antibody against the epitope, for example.

An "immunoassay" as used herein, refers to any measurement of the specific binding reaction between an antigen and an immunoglobulin, such as an antibody. Typically the antigen is an (poly)peptide or protein, but any other substance, such as a nucleic acid, a lipid, a fatty acid or a small organic molecule, may serve as an antigen. The skilled artisan will easily understand and determine which immunoassay is best suited to measure the specific binding between an antigen and an immunoglobulin.

The term "a representative sample" as used in the context of the present invention relates to a representative sample of variable light (VL) and variable heavy (VH) chains of the immunoglobulins of a sample that need to be sequenced in order to get an overview of the variable light (VL) and variable heavy (VH) chains of the immunoglobulins present in said sample. The total number of the sequences required to get such an overview may depend from the nature of the respective sample, but should at least be so high, that a reasonable estimation can be made which variable light (VL) chains and which variable heavy (VH) chains of the immunoglobulins ar most abundant in said sample. Preferably at least 20%, at least 30%, at least 40%, at least 50%, at least 60%, at least 70%, at least 80%, at least 90% or at least 95% of the variable light (VL) and the variable heavy (VH) chains of the immunoglobulins present in said sample are sequenced. Also preferably at least 1,000, at least 10,000, at least 50,000, or at least 100,000 of the variable light (VL) and the variable heavy (VH) chains of the immunoglobulins present in said sample are sequenced.

The term "most abundant" as used in the context of the present invention refers to those variable light (VL) and variable heavy (VH) chains that are identified most frequently when a sample is sequenced. The most abundant variable light (VL) and variable heavy (VH) chains are typically those which are present in the highest number in a certain sample.

In certain embodiments the present invention provides a method for the identification of an antibody, a target, or an agent in a sample, comprising:

a) obtaining cDNAs of mRNAs encoding immunoglobulins in the sample, thereby obtaining a mixture of the cDNAs;

b) sequencing at least a representative sample of the variable heavy (VH) and variable light (VL) chains of the immunoglobulins, thereby obtaining sequence data of the VH and VL chains of the immunoglobulins (IgGs) present in the sample;

c) determining the most abundant VH and VL chains present in the sample using a computer-implemented algorithm;

d) synthesizing polynucleotides of the most abundant VH and VL chains and producing antibodies comprising said VH and VL chains using a mammalian expression vector; and e) testing the antibodies, thereby identifying the antibody or the target.

Preferably said sample is a biological sample. Preferably said biological sample is from a mammal. Preferably said mammal is a human, murine, rodent, mouse, rat, squirrel, chipmunk, gopher, porcupine, beaver, hamster, gerbil, guinea pig, rabbit, dog, cat, cow, or horse. Preferably said human is a cancer patient, said human is immunized or said human is infected with an agent or a target molecule. Preferably the mRNAs encoding said immunoglobulins in the sample are obtained by harvesting or isolating B-cells from the sample. Preferably said immunoglobulins are of the class IgG. Preferably the cDNAs obtained from the mRNAs encoding immunoglobulins in the sample are generated by reverse transcriptase-PCR. Preferably IgG specific primers are used for the generation of the cDNAs from the mRNAs encoding the immunoglobulins. Preferably the VH and VL chains present in the sample are determined by analyzing sequence data of the VH and VL chains present in the sample. Most preferably, the methods of the present invention do not require any cloning steps. In particular all steps of the method performed up to the determination of the most abundant VH and VL chains present in the sample using a computer-implemented algorithm do not require any cloning steps. Preferably the VH and VL polynucleotides of the most abundant VH and VL chains in step (d) are integrated into a mammalian expression vector. Preferably the antibodies produced in said step (e) are released into the culture medium. Preferably the testing of the antibodies in step (e) of the method is carried out by employing an immunoassay. Preferably the in step (e) of the method an antibody is identified which binds to a certain target molecule or tissue. Preferably in step (e) of the method a target molecule is identified which binds to a certain antibody.

In certain embodiments the present invention provides a method for the identification of an antibody, a target, or an agent comprising:

a) providing a biological sample from a mammal that is immunized, infected with an agent or a target molecule or suffers from cancer;

b) harvesting B-cells from the biological sample;

c) obtaining mRNAs from the harvested B-cells;

d) generating cDNAs of the immunoglobulins encoded by the mRNA, thereby obtaining a mixture of the cDNAs;

e) sequencing at least a representative sample of the variable heavy (VH) and variable light (VL) chains of the immunoglobulins, thereby obtaining sequence data of the VH and VL chains of the immunoglobulins present in the sample;

f) determining the most abundant VH and VL chains present in the sample using a computer-implemented algorithm;

h) synthesizing polynucleotides of the most abundant VH and VL chains;

i) integrating the synthesized VH and VL polynucleotides into a mammalian expression vector;

j) allowing the VH and VL polynucleotides-integrated vectors to express the VH and VL polynucleotides, thereby producing antibodies; and k) testing the antibodies by using an immunoassay, thereby identifying the antibody, target, or the agent. Preferably said sample is a biological sample. Preferably said biological sample is from a mammal. Preferably said mammal is a human, murine, rodent, mouse, rat, squirrel, chipmunk, gopher, porcupine, beaver, hamster, gerbil, guinea pig, rabbit, dog, cat, cow, or horse. Preferably said human is a cancer patient, said human is immunized or said human is infected with an agent or a target molecule. Preferably said the immunoglobulins are of the class IgG.

In certain embodiments the present invention provides a method for the identification of an antibody, a target, or an agent in a sample comprising the steps of:

a) analyzing the sequence data of the VH and VL chains present in the sample; and b) determining the abundance of VH and VL chains present in the sample. Preferably said method further comprises preparing one or more immunoglobulins containing abundant VH and VL chains identified in step b). Preferably said sample is a biological sample. Preferably said biological sample is from a mammal. Preferably said mammal is a human, murine, rodent, mouse, rat, squirrel, chipmunk, gopher, porcupine, beaver, hamster, gerbil, guinea pig, rabbit, dog, cat, cow, or horse. Preferably said human is a cancer patient, said human is immunized or said human is infected with an agent or a target molecule. Preferably said the immunoglobulins are of the class IgG.

In certain embodiments the present invention provides a method of identifying an antibody, a target, or an agent in a sample comprising the steps of:
a) obtaining cDNAs of mRNAs encoding immunoglobulins in the sample, thereby obtaining a mixture of the cDNAs;
b) directly sequencing at least a representative sample of the variable heavy (VH) and variable light (VL) chains of the immunoglobulins, thereby obtaining sequence data of the VH and VL chains of the immunoglobulins present in the sample;
c) determining the most abundant VH and VL chains present in the sample using a computer-implemented algorithm;
d) synthesizing polynucleotides encoding the most abundant VH and VL chains present in the sample and producing antibodies comprising said VH and VL chains using an expression vector; and
e) testing the antibodies, thereby identifying the antibody or the target.

The term "direct sequencing" as used in the context of step (b) of the method recited above refers to a situation where the cDNAs obtained in step (a) are sequenced without any additional molecular biological modification steps. In particular no cloning steps are required.

In preferred embodiments the sample is a biological sample. In more preferred embodiments the biological sample is from a mammal. Said mammal may be a human, murine, rodent, mouse, rat, squirrel, chipmunk, gopher, porcupine, beaver, hamster, gerbil, guinea pig, rabbit, dog, cat, cow, or horse. Said biological sample may also be from a human, wherein said human is a cancer patient, said human is immunized or said human is infected with an agent or a target molecule.

In preferred embodiments the mRNAs encoding immunoglobulins in step (a) of the method recited above are obtained by harvesting or isolating B-cells from the sample. In other preferred embodiments the immunoglobulins are of the class IgG.

In preferred embodiments the cDNAs of the mRNAs encoding immunoglobulins in step (a) of the method recited above are generated by reverse transcriptase-PCR. In more preferred embodiments IgG specific primers are used in said reverse transcriptase-PCR.

In preferred embodiments the most abundant VH and VL chains present in the sample in step (c) of the method recited above are determined by analyzing sequence data of the VH and VL chains present in the sample.

In preferred embodiments steps (a)-(c) of the method recited above does not require any cloning steps.

In preferred embodiments the VH and VL polynucleotides synthesized in step (d) of the method recited above are integrated into an expression vector. More preferably said expression vector is a mammalian expression vector.

In preferred embodiments the antibodies produced in step (d) of the method recited above are released into the culture medium.

In preferred embodiments the testing of the antibodies in step (e) of the method recited above is carried out by employing an immunoassay.

In preferred embodiments in step (e) of the method recited above an antibody is identified which binds to a certain target molecule or tissue. In other preferred embodiments in step (e) of the method recited above a target molecule is identified which binds to a certain antibody.

In certain embodiments the present invention provides a method of identifying an antibody, a target, or an agent comprising the steps of:
a) providing a biological sample from a mammal that is immunized, infected with an agent or a target molecule or suffers from cancer;
b) harvesting B-cells from the biological sample;
c) obtaining mRNAs from the harvested B-cells;
d) generating cDNAs of the immunoglobulins encoded by the mRNA, thereby obtaining a mixture of the cDNAs;
e) directly sequencing at least a representative sample of the variable heavy (VH) and variable light (VL) chains of the immunoglobulins, thereby obtaining sequence data of the VH and VL chains of the immunoglobulins present in the sample;
f) determining the most abundant VH and VL chains present in the sample using a computer-implemented algorithm;
h) synthesizing polynucleotides encoding the most abundant VH and VL chains present in the sample;
i) integrating the synthesized VH and VL polynucleotides into a mammalian expression vector;
j) allowing the VH and VL polynucleotides-integrated vectors to express the VH and VL polynucleotides, thereby producing antibodies; and
k) testing the antibodies by using an immunoassay, thereby identifying the antibody, target, or the agent. In preferred embodiments said sample is a biological sample. In more preferred embodiments said biological sample is from a mammal. Said mammal can be a human, murine, rodent, mouse, rat, squirrel, chipmunk, gopher, porcupine, beaver, hamster, gerbil, guinea pig, rabbit, dog, cat, cow, or horse. In more preferred embodiments said human is a cancer patient, said human is immunized or said human is infected with an agent or a target molecule. In more preferred embodiments the immunoglobulins are of the class IgG.

In certain embodiments the present invention provides a method of identifying an antibody, a target, or an agent in a sample comprising the steps of:
a) analyzing the sequence data of the VH and VL chains present in the sample; and
b) determining the abundance of VH and VL chains present in the sample. In further embodiments said method further comprises preparing one or more immunoglobulins containing abundant VH and VL chains identified in step b). In preferred embodiments said sample is a biological sample. In more preferred embodiments said biological sample is from a mammal. Said mammal can be a human, murine, rodent, mouse, rat, squirrel, chipmunk, gopher, porcupine, beaver, hamster, gerbil, guinea pig, rabbit, dog, cat, cow, or horse. In more preferred embodiments said human is a cancer patient, said human is immunized or said human is infected with an agent or a target molecule. In more preferred embodiments the immunoglobulins are of the class IgG.

This disclosure is further described by the following examples, which do not limit the scope of the disclosure in any manner.

EXAMPLES

Harvesting B-Cells from an Immunized/Infected Patient:

B-Cells can be isolated from immunized or infected patients in various different ways, an such techniques are known to the skilled artisan. In many such techniques resting B lymphocytes (B cells) are isolated from spleens by using negative selection with anti-CD43 and anti-Mac-1/CD11b monoclonal antibodies, e.g. via magnetic microbeads. This strategy depletes non-B cells from a mixed population of splenocytes and relies on the fact that most mature leukocytes, with the exception of resting splenic B cells, express CD43 (in fact, expression of CD43 has been demonstrated on immature B cells, plasma cells, and some mature B1 cells, in addition to granulocytes, monocytes, macrophages, platelets, natural killer (NK) cells, thymocytes, and peripheral CD8pos and most CD4pos T cells). Anti-Mac-1/CD11b microbeads are included in the negative selection to improve the removal of myeloid cells. B-cell isolation may be automated by using an AutoMACS automatic magnetic bead cell sorter (Miltenyi Biotec). As assessed by fluorescence analysis of B220+ cells, such isolation routinely yields approximately $4 \times 10e7$ B cells per spleen that are >95% pure. See also Miltenyi S, Muller W, Weichel W, and Radbruch A. (1990) Cytometry 11 (2), 231-238.

mRNA extraction and Reverse Transcription:

Immunoglobulins, preferably immunoglobulins of the IgG type, can be selectively amplified from B cells via mRNA extraction followed by reverse transcription.

mRNA extraction from eucaryotic cells, such as B cells, is a well know technological procedure. Numerous protocols exist and commercial kits are available. Such as the PolyATtract® mRNA Isolation System (Promega, Madison, Wis., USA) or various RNeasy and Oligotex DirectmRNA kits (both from Qiagen, Hilden, Germany). Many of these techniques make use of the polyA tail of the eukaryotic mRNA, e.g. via affinity purification to oligo (dT) matrices, such as oligo (dT) cellulose.

Immunoglobulins can be selective amplified from the isolated mRNA via reverse transcription using specific primers, followed by conventional PCR. The specific primers may be specific for immunoglobulins, for a certain immunoglobuline class, i.e. either IgG, IgM, IgA, IgD or IgE, or even for a certain immunoglobulin sub-class, such as IgG1, IgG2, IgG3 or IgG4. Primers that may be used to amplify immunoglobuling heavy and light chain genes are for example disclosed in Cancer Surv 1997; 30:21-44, J Clin Pathol 1994; 47:493-6, J Clin Pathol 1990; 43:888-90 or Mol Pathol. 2002 April; 55(2): 98-101.

Genomic Sequencing of the cDNAs:

The complete sequences of the immunoglobulins are sequenced. Various companies exist which are able to sequence entire genomes, such as Helicos BioSciences Corporation (Cambridge, Mass., USA). With its True Single Molecule Sequencing™ technology Helicos is able to directly sequence single molecules of DNA or RNA at high speed and efficiency. Other companies able to perform similar sequence endeavors include Illumina (San Diego, Calif., USA; Solexa system) and Roche (Basel, CH; 454 system). No cloning steps are required prior to sequencing.

Sequences of the VH and the VL chains of the immunoglobulins are determined separately. More than $10^3$ independent sequences of the VH and the VL chains are determined, preferably more than $10^4$ independent sequences, more preferably more than $10^5$ independent sequences, and even more preferably more than $10^6$ independent sequences.

The sequences determined may be stored in any database system. Such database systems may be part of sequencing system used. Alternatively, the sequence information may also be stored in any other format, such as in the form of an Excel spreadsheet or in tab-delimited format.

Determination of Dominant/Abundant VH and VL Sequences Based on Pre-Determined Algorithm:

Abundance of the VH and VL chains of the sequenced immunoglobulins can be determined by various algorithms. VH chains and VL chains are preferably analyzed separately.

A first step may be to identify sequences of the VH and VL chains which derive from the same immunoglobulins. Sequences which derive from the same immunoglobulins are not necessarily completely identical. Such minor differences may arise because the sequences do not begin or end at the very same nucleotides for each sequence, or because a nucleotide was misread in the sequencing process, an event which can happen during such large scale sequencing projects. It is known that certain nucleotides, and in particular certain sequences of nucleotides are more prone to be misread than others (e.g. GC-rich nucleotide stretches). Bioinformatic tools and algorithms, many of which are part of the respective sequencing systems are able to determine such occasions, or at least to point to instances, at which such errors might have occurred.

The abundance of the VH and VL chains may be determined by various statistical tests. In its easiest from the individual VH and VL chains are simply counted. More sophisticated statistical tests may take various other parameters into account. By way of non-limiting examples, the following statistical tests and references may guide as examples of the numerous approaches that have been made in such, or similar, analysis: Bayesian Shrinkage Estimation (see e.g. Biometrics 59 (2003): 476-486), DADA (Digital Analysis of cDNA Abundance, see e.g. BMC Genomics 2002, 3:7), linear modeling (Pacific Symposium on Biocomputing, 1999, 4:41-52) and various clustering methods (BMC Bioinformatics 2006, 7:397, Fourth IEEE International Conference on Data Mining (ICDM'04), pp. 403-406).

Synthesis of VH and VL:

Genes of the most abundant VH and VL chains are synthesized by customary means. Such synthesis is standard technology and many companies offer respective services, e.g. Entelechon (Regensburg, Germany), Geneart (Regensburg, Germany) or Sloning Biotechnology (Puchheim, Germany), to name a few. Ideally the respective genes already carry appropriate restriction sites for cloning into appropriate vectors.

Cloning and Expression of the Dominant VH and VL Chains:

The synthesized genes of the VH and the VL chains are cloned into respective expression vectors. To do so the respective expression vector is digested with appropriate restriction enzymes which are compatible with the synthesized genes. As outlined above, the synthesized genes are preferably already compatible with the vector, i.e. respective restriction sites are already present in the synthesized genes. Exemplary vectors include pcDNA, pMORPH, pUC, pBR, pBAD and others. Expression from the vectors leads to the production of full-length immunoglobulins comprising the synthesized VH and VL chains, which can be further characterized or modified in subsequent steps.

Immunoassays for Screening the Expressed Polypeptides and Selection of VH And VL Pairs Full-length immunoglobulins produced after expression from respective vectors, such as pcDNA, pMORPH, pUC, pBR, pBAD and others can be used for various types of assays. For example, immunoassays may be performed.

For example, binding of the immunoglobulins to a certain target molecule, such as an antigen may be assayed. This may be accomplished by standard laboratory procedures, such as ELISA tests, Western Blotting or any other equivalent means. Such experiments may lead to the identification of those immunoglobulins which bind to a certain target molecule. Such tests may also be performed in a more quantitative manner, i.e. it is not just determined whether or not a respective immunoglobulin binds to a certain target molecule, but also how strong such an interaction occurs. This may be achieved via the determination of the binding affinity, the dissociation constant, or any other equivalent parameter, of an immunoglobulin to a given target molecule. Respective techniques include surface plasmon resonance, solution equilibrium titration, cantilever, acoustic biosensor and other methods known in the art.

It is also possible to identify the target molecule to which a given immunoglobulin binds. In order to do so a certain immunoglobulin is chosen and subjected to a mixture of potential binding proteins under conditions which allow binding of the immunoglobulin to at least one target molecule of the mixture. The respective binding conditions may be adjusted by appropriate selection of parameters, such as buffer composition and stringency.

Identification of Target/Antibody:

Identification of the immunoglobulin which binds to a given target molecule, or identification of the target molecule which binds to a given immunoglobulin, can be accomplished by any known methodology. Many such methods are known to the skilled artisan and as exemplary references the following are provided: Valle R P, Curr Opin Drug Discov Devel. 2003 March; 6(2):197-203; Ackermann B L Expert Rev Proteomics. 2007 April; 4(2):175-86; and Anderson K S J Proteome Res. 2005 July-August; 4(4):1123-33

It is to be understood that the description, specific examples and data, while indicating exemplary embodiments, are given by way of illustration and are not intended to limit the disclosure. Various changes and modifications within this disclosure will become apparent to the skilled artisan from the discussion, disclosure and data contained herein, and thus are considered part of this disclosure.

What is claimed is:

1. A method of identifying an antibody, or a target, comprising the steps of:
   a) obtaining a sample of at least $10^6$ B cells from an immunized mammal, extracting mRNAs encoding immunoglobulins from the B cells, and reverse transcribing cDNAs of the mRNAs, thereby obtaining a mixture of the cDNAs;
   b) using single, massive parallel sequencing technology to directly parallel sequence within 24 hours, without any prior cloning steps, the cDNAs encoding the variable heavy (VH) and variable light (VL) chains of the immunoglobulins from the sample, thereby obtaining sequence data of the VH and VL chains of the immunoglobulins present in the sample;
   c) determining the frequency of the VH and VL chain sequences present in the sample by counting or statistical analysis,
   d) identifying the most abundant VH and VL chain sequences present in the sample according to their frequency;
   e) synthesizing polynucleotides encoding the most abundant VH and VL chain sequences present in the sample and producing antibodies comprising said VH and VL chains by cloning the polynucleotides into an expression vector, introducing the expression vector into a host cell and expressing the antibodies; and
   f) identifying the antibody(ies) specific for a target of interest or identifying the target molecule to which the antibody(ies) is specific.

2. The method of claim 1, wherein the sample is a biological sample.

3. The method of claim 1, wherein said mammal is a human, murine, rodent, mouse, rat, squirrel, chipmunk, gopher, porcupine, beaver, hamster, gerbil, guinea pig, rabbit, dog, cat, cow, or horse.

4. The method of claim 3, wherein said human is a cancer patient, said human is immunized or said human is infected with an agent or a target molecule.

5. The method of claim 1, wherein the mRNAs encoding immunoglobulins are obtained by harvesting or isolating B-cells from the sample.

6. The method of claim 1, wherein the immunoglobulins are of the class IgG.

7. The method of claim 1, wherein step (a) further comprises amplifying the mixture of cDNAs of the mRNAs encoding immunoglobulins by reverse transcriptase-PCR.

8. The method of claim 7, wherein IgG specific primers are used.

9. The method of claim 1, wherein said expression vector is a mammalian expression vector.

10. The method of claim 1, wherein the antibodies produced in step e) are expressed into a culture medium.

11. The method of claim 1, wherein the identifying the antibodies specific for a target of interest in step f) is carried out by immunoassay.

12. The method of claim 1, wherein the obtaining of step a) comprises the steps of:
   aa) providing a biological sample from a mammal that is immunized, infected with an agent or a target molecule or suffers from cancer;
   ab) harvesting B-cells from the biological sample;
   ac) obtaining mRNAs from the harvested B-cells;
   ad) generating cDNAs of the immunoglobulins encoded by the mRNA, thereby obtaining a mixture of the cDNAs; and wherein step e) further comprises the steps of:
   da) integrating the synthesized VH and VL polynucleotides into a mammalian expression vector and introducing the expression vector into a mammalian host cell; and
   db) allowing the host cells to express the VH and VL polynucleotides, thereby producing antibodies.

* * * * *